(12) United States Patent
Layman et al.

(10) Patent No.: US 8,376,961 B2
(45) Date of Patent: Feb. 19, 2013

(54) MICROMACHINED COMPOSITE GUIDEWIRE STRUCTURE WITH ANISOTROPIC BENDING PROPERTIES

(75) Inventors: Ted W. Layman, Park City, UT (US); Clay W. Northrop, Salt Lake City, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 935 days.

(21) Appl. No.: 12/099,014

(22) Filed: Apr. 7, 2008

(65) Prior Publication Data

US 2009/0254000 A1    Oct. 8, 2009

(51) Int. Cl.
*A61M 25/00* (2006.01)
*A61M 25/09* (2006.01)

(52) U.S. Cl. ........................................ 600/585; 600/434
(58) Field of Classification Search .................. 600/434, 600/585
See application file for complete search history.

(56) References Cited

U.S. PATENT DOCUMENTS

| | | |
|---|---|---|
| 1,553,227 A | 9/1925 | Feyk et al. |
| 1,866,888 A | 7/1932 | Hawley |
| 2,275,827 A | 3/1942 | Plensler |
| 2,413,805 A | 1/1947 | Vickers |
| 2,441,166 A | 5/1948 | Raspert |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |

(Continued)

FOREIGN PATENT DOCUMENTS

| | | |
|---|---|---|
| AU | 723040 | 12/1997 |
| AU | 733966 | 4/1998 |
| BR | PI 9712829 | 1/2000 |
| CA | 2266685 | 5/2006 |
| CA | 2255781 | 3/2007 |

(Continued)

OTHER PUBLICATIONS

"Mechanical Design and Systems Handbook", H.A. Rothbart, 1964, p. 33-13 (one sheet).

*Primary Examiner* — Sean Dougherty
(74) *Attorney, Agent, or Firm* — Seager, Tufte & Wickhem, LLC

(57) ABSTRACT

Medical devices and methods for making and using the same. An example medical device may include an elongate core member having a proximal portion and a distal portion. The distal portion may include a distal end and a flattened region. The flattened region may be disposed proximally of the distal end. The flattened region may have a height and a width. The width may be twice or more as large as the height. A tubular member may be disposed over the distal portion. The tubular member may have a plurality of slots formed therein.

14 Claims, 7 Drawing Sheets

U.S. PATENT DOCUMENTS

| | | |
|---|---|---|
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Wilson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,676,249 A | 6/1987 | Arenas et al. |
| 4,721,117 A | 1/1988 | Mar et al. |
| 4,737,153 A | 4/1988 | Shimamura et al. |
| 4,748,986 A * | 6/1988 | Morrison et al. ............ 600/585 |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gamble |
| 5,065,769 A | 11/1991 | De Toledo |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,318,529 A | 6/1994 | Kontos |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,354,623 A | 10/1994 | Hall |
| 5,358,479 A * | 10/1994 | Wilson ....................... 604/95.04 |
| 5,358,493 A | 10/1994 | Schweich et al. |
| 5,358,796 A | 10/1994 | Nakamura et al. |
| 5,365,942 A | 11/1994 | Shank |
| 5,365,943 A | 11/1994 | Jansen |
| 5,368,564 A | 11/1994 | Savage |
| 5,368,661 A | 11/1994 | Nakamura et al. |
| 5,376,084 A | 12/1994 | Bacich et al. |
| 5,381,782 A | 1/1995 | DeLaRama et al. |
| 5,406,960 A | 4/1995 | Corso, Jr. |
| 5,409,015 A * | 4/1995 | Palermo ........................ 600/585 |
| 5,411,476 A | 5/1995 | Abrams |
| 5,433,200 A * | 7/1995 | Fleischhacker, Jr. ......... 600/434 |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,465,732 A * | 11/1995 | Abele ........................... 600/585 |
| 5,470,330 A | 11/1995 | Goldenberg et al. |
| 5,476,701 A | 12/1995 | Berger |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirzaee et al. |
| 5,622,184 A | 4/1997 | Ashby et al. |
| 5,630,806 A | 5/1997 | Inagaki et al. |
| 5,636,642 A * | 6/1997 | Palermo ........................ 600/585 |

| | | | | | | |
|---|---|---|---|---|---|---|
| 5,637,089 A | 6/1997 | Abrams et al. | | 6,214,042 B1 | 4/2001 | Jacobsen et al. |
| 5,656,011 A | 8/1997 | Uihlein et al. | | 6,228,073 B1 | 5/2001 | Noone et al. |
| 5,658,264 A | 8/1997 | Samson et al. | | 6,248,082 B1 | 6/2001 | Jafari |
| 5,666,968 A | 9/1997 | Imran et al. | | 6,251,092 B1 | 6/2001 | Qin et al. |
| 5,666,969 A | 9/1997 | Urick et al. | | 6,254,549 B1 | 7/2001 | Ramzipoor |
| 5,669,926 A | 9/1997 | Aust et al. | | 6,260,458 B1 | 7/2001 | Jacobsen et al. |
| 5,676,659 A | 10/1997 | McGurk | | 6,273,404 B1 | 8/2001 | Holman et al. |
| 5,676,697 A | 10/1997 | McDonald | | 6,273,876 B1 | 8/2001 | Klima et al. |
| 5,682,894 A | 11/1997 | Orr et al. | | 6,273,879 B1 | 8/2001 | Keith et al. |
| 5,690,120 A | 11/1997 | Jacobsen et al. | | 6,290,656 B1 | 9/2001 | Boyle et al. |
| 5,720,300 A | 2/1998 | Fagan et al. | | 6,296,616 B1 | 10/2001 | McMahon |
| 5,722,609 A | 3/1998 | Murakami | | 6,296,631 B2 | 10/2001 | Chow |
| 5,728,063 A | 3/1998 | Preissman et al. | | 6,302,870 B1 | 10/2001 | Jacobsen et al. |
| 5,741,429 A | 4/1998 | Donadio, III et al. | | 6,325,790 B1 | 12/2001 | Trotta |
| 5,746,701 A | 5/1998 | Noone | | 6,338,725 B1 | 1/2002 | Hermann et al. |
| 5,769,796 A * | 6/1998 | Palermo et al. ............... 600/585 | | 6,346,091 B1 | 2/2002 | Jacobsen et al. |
| 5,769,830 A | 6/1998 | Parker | | 6,352,515 B1 | 3/2002 | Anderson et al. |
| 5,772,609 A | 6/1998 | Nguyen et al. | | 6,355,005 B1 | 3/2002 | Powell et al. |
| 5,782,809 A | 7/1998 | Umeno et al. | | 6,355,027 B1 | 3/2002 | Le et al. |
| 5,788,653 A | 8/1998 | Lorenzo | | 6,368,315 B1 | 4/2002 | Gillis et al. |
| 5,788,654 A | 8/1998 | Schwager | | 6,368,316 B1 | 4/2002 | Jansen et al. |
| 5,788,707 A | 8/1998 | Del Toro et al. | | 6,375,628 B1 | 4/2002 | Zadno-Azizi et al. |
| 5,792,124 A | 8/1998 | Horrigan et al. | | 6,375,774 B1 | 4/2002 | Lunn et al. |
| 5,797,856 A | 8/1998 | Frisbie et al. | | 6,379,369 B1 | 4/2002 | Abrams et al. |
| 5,800,454 A | 9/1998 | Jacobsen et al. | | 6,387,060 B1 * | 5/2002 | Jalisi ............................ 600/585 |
| 5,807,075 A | 9/1998 | Jacobsen et al. | | 6,390,993 B1 | 5/2002 | Cornish et al. |
| 5,807,249 A | 9/1998 | Qin et al. | | 6,398,758 B1 | 6/2002 | Jacobsen et al. |
| 5,810,885 A | 9/1998 | Zinger | | 6,428,489 B1 | 8/2002 | Jacobsen et al. |
| 5,813,996 A | 9/1998 | St. Germain et al. | | 6,428,512 B1 | 8/2002 | Anderson et al. |
| 5,827,225 A | 10/1998 | Ma Schwab | | 6,431,039 B1 | 8/2002 | Jacobsen et al. |
| 5,827,242 A | 10/1998 | Follmer et al. | | 6,440,088 B1 | 8/2002 | Jacobsen |
| 5,833,632 A | 11/1998 | Jacobsen et al. | | 6,478,778 B1 | 11/2002 | Jacobsen et al. |
| 5,836,926 A | 11/1998 | Peterson et al. | | 6,488,637 B1 | 12/2002 | Eder et al. |
| 5,843,050 A | 12/1998 | Jones et al. | | 6,491,648 B1 | 12/2002 | Cornish et al. |
| 5,843,244 A | 12/1998 | Pelton et al. | | 6,491,671 B1 | 12/2002 | Larson, III et al. |
| 5,851,203 A | 12/1998 | van Muiden | | 6,503,244 B2 | 1/2003 | Hayman |
| 5,895,378 A | 4/1999 | Nita | | 6,508,803 B1 | 1/2003 | Horikawa et al. |
| 5,897,537 A | 4/1999 | Berg et al. | | 6,524,301 B1 | 2/2003 | Wilson et al. |
| 5,902,254 A | 5/1999 | Magram | | 6,530,934 B1 | 3/2003 | Jacobsen et al. |
| 5,902,290 A | 5/1999 | Peacock, III et al. | | 6,547,779 B2 | 4/2003 | Levine et al. |
| 5,904,657 A | 5/1999 | Unsworth et al. | | 6,553,880 B2 | 4/2003 | Jacobsen et al. |
| 5,906,618 A | 5/1999 | Larson, III | | 6,556,873 B1 | 4/2003 | Smits |
| 5,911,715 A | 6/1999 | Berg et al. | | 6,579,246 B2 | 6/2003 | Jacobsen et al. |
| 5,911,717 A | 6/1999 | Jacobsen et al. | | 6,602,207 B1 | 8/2003 | Mam et al. |
| 5,916,177 A | 6/1999 | Schwager | | 6,602,280 B2 | 8/2003 | Chobotov |
| 5,916,178 A | 6/1999 | Noone | | 6,610,046 B1 | 8/2003 | Usami et al. |
| 5,916,194 A | 6/1999 | Jacobsen et al. | | 6,623,448 B2 | 9/2003 | Slater |
| 5,931,830 A | 8/1999 | Jacobsen et al. | | 6,636,758 B2 | 10/2003 | Sanchez et al. |
| 5,935,108 A | 8/1999 | Katoh et al. | | 6,638,266 B2 | 10/2003 | Wilson et al. |
| 5,947,940 A | 9/1999 | Beisel | | 6,652,508 B2 | 11/2003 | Griffin et al. |
| 5,951,539 A | 9/1999 | Nita et al. | | 6,669,670 B1 | 12/2003 | Muni et al. |
| 5,957,865 A * | 9/1999 | Backman et al. ............. 600/585 | | 6,682,493 B2 | 1/2004 | Mirigian |
| 5,971,975 A | 10/1999 | Mills et al. | | 6,689,120 B1 | 2/2004 | Gerdts |
| 5,980,471 A | 11/1999 | Jafari | | 6,702,762 B2 | 3/2004 | Jafari et al. |
| 6,001,068 A | 12/1999 | Uchino et al. | | 6,712,826 B2 | 3/2004 | Lui |
| 6,004,279 A | 12/1999 | Crowley et al. | | 6,730,095 B2 | 5/2004 | Olson, Jr. et al. |
| 6,014,919 A | 1/2000 | Jacobsen et al. | | 6,740,050 B2 * | 5/2004 | D'Aquanni et al. .......... 600/585 |
| 6,017,319 A | 1/2000 | Jacobsen et al. | | 6,749,560 B1 | 6/2004 | Konstorum et al. |
| 6,022,343 A | 2/2000 | Johnson et al. | | 6,766,720 B1 | 7/2004 | Jacobsen et al. |
| 6,022,369 A | 2/2000 | Jacobsen et al. | | 6,777,644 B2 | 8/2004 | Peacock, III et al. |
| 6,024,730 A | 2/2000 | Pagan | | 6,811,544 B2 | 11/2004 | Schaer |
| 6,027,461 A | 2/2000 | Walker et al. | | 6,866,642 B2 | 3/2005 | Kellerman et al. |
| 6,042,553 A | 3/2000 | Solar et al. | | 6,887,235 B2 | 5/2005 | O'Connor et al. |
| 6,045,547 A | 4/2000 | Ren et al. | | 6,918,882 B2 | 7/2005 | Skujins et al. |
| 6,048,339 A | 4/2000 | Zirps et al. | | 6,997,937 B2 | 2/2006 | Jacobsen et al. |
| 6,056,702 A | 5/2000 | Lorenzo | | 7,001,369 B2 | 2/2006 | Griffin et al. |
| 6,063,101 A | 5/2000 | Jacobsen et al. | | 7,074,197 B2 | 7/2006 | Reynolds et al. |
| 6,063,200 A | 5/2000 | Jacobsen et al. | | 7,083,577 B2 * | 8/2006 | Osawa et al. .................. 600/585 |
| 6,066,361 A | 5/2000 | Jacobsen et al. | | 7,153,277 B2 | 12/2006 | Skujins et al. |
| 6,106,485 A | 8/2000 | McMahon | | 7,169,118 B2 | 1/2007 | Reynolds et al. |
| 6,106,488 A | 8/2000 | Fleming et al. | | 7,182,735 B2 | 2/2007 | Shireman et al. |
| 6,139,510 A | 10/2000 | Palermo | | 7,455,646 B2 * | 11/2008 | Richardson et al. .......... 600/585 |
| 6,165,292 A | 12/2000 | Abrams et al. | | 2001/0007927 A1 * | 7/2001 | Koblish et al. ................ 600/585 |
| 6,171,296 B1 | 1/2001 | Chow | | 2002/0019599 A1 | 2/2002 | Rooney et al. |
| 6,183,410 B1 | 2/2001 | Jacobsen et al. | | 2003/0009208 A1 | 1/2003 | Snyder et al. |
| 6,193,686 B1 | 2/2001 | Estrada et al. | | 2003/0060732 A1 | 3/2003 | Jacobsen et al. |
| 6,197,014 B1 | 3/2001 | Samson et al. | | 2003/0069522 A1 | 4/2003 | Jacobsen et al. |
| 6,203,485 B1 | 3/2001 | Urick | | 2003/0216668 A1 | 11/2003 | Howland et al. |
| RE37,148 E | 4/2001 | Shank | | 2003/0229298 A1 * | 12/2003 | Iwami et al. .................. 600/585 |

| Publication No. | Date | Name |
|---|---|---|
| 2004/0111044 A1 | 6/2004 | Davis et al. |
| 2004/0116831 A1 | 6/2004 | Vrba |
| 2004/0142643 A1 | 7/2004 | Miller et al. |
| 2004/0167437 A1 | 8/2004 | Sharrow et al. |
| 2004/0167441 A1 | 8/2004 | Reynolds et al. |
| 2004/0181174 A2 | 9/2004 | Davis et al. |
| 2006/0116609 A1* | 6/2006 | Kanuka et al. .............. 600/585 |
| 2006/0121218 A1 | 6/2006 | Obara et al. |
| 2006/0122537 A1 | 6/2006 | Reynolds et al. |
| 2006/0189896 A1 | 8/2006 | Davis et al. |
| 2006/0264784 A1* | 11/2006 | Lupton ......................... 600/585 |
| 2006/0264904 A1 | 11/2006 | Kerby et al. |
| 2007/0032746 A1* | 2/2007 | Sell ............................... 600/585 |
| 2007/0244413 A1* | 10/2007 | Biggins ........................ 600/585 |
| 2007/0287955 A1* | 12/2007 | Layman et al. ........... 604/93.01 |
| 2008/0021347 A1 | 1/2008 | Jacobsen et al. |
| 2008/0021348 A1 | 1/2008 | Jacobsen et al. |
| 2008/0021400 A1 | 1/2008 | Jacobsen et al. |
| 2008/0021401 A1 | 1/2008 | Jacobsen et al. |
| 2008/0021402 A1 | 1/2008 | Jacobsen et al. |
| 2008/0021403 A1 | 1/2008 | Jacobsen et al. |
| 2008/0021404 A1 | 1/2008 | Jacobsen et al. |
| 2008/0021405 A1 | 1/2008 | Jacobsen et al. |
| 2008/0021406 A1 | 1/2008 | Jacobsen et al. |
| 2008/0021407 A1 | 1/2008 | Jacobsen et al. |
| 2008/0021408 A1 | 1/2008 | Jacobsen et al. |
| 2008/0077049 A1 | 3/2008 | Hirshman |
| 2008/0077119 A1 | 3/2008 | Snyder et al. |
| 2009/0036834 A1* | 2/2009 | Voeller et al. ............. 604/164.13 |

FOREIGN PATENT DOCUMENTS

| | | |
|---|---|---|
| CN | 1230914 | 10/1999 |
| DE | 2539191 | 3/1976 |
| DE | 285514 | 12/1990 |
| EP | 0 045 931 | 2/1982 |
| EP | 0 069 522 | 1/1983 |
| EP | 0 087 933 | 9/1983 |
| EP | 0 111 044 | 6/1984 |
| EP | 0 181 174 | 5/1986 |
| EP | 0 377 453 | 7/1990 |
| EP | 0 565 065 | 6/1996 |
| EP | 0 778 038 | 6/1997 |
| EP | 0 778 039 | 6/1997 |
| EP | 0 778 040 | 6/1997 |
| EP | 0 812 599 | 12/1997 |
| EP | 0 865 772 | 9/1998 |
| EP | 0 865 773 | 9/1998 |
| EP | 0 521 595 | 5/1999 |
| EP | 0 917 885 | 5/1999 |
| EP | 0 937 481 | 8/1999 |
| EP | 0 790 066 | 4/2000 |
| EP | 0 608 853 | 4/2003 |
| EP | 0 935 947 | 12/2004 |
| EP | 0 934 141 | 11/2005 |
| EP | 1709987 | 10/2006 |
| GB | 2214354 | 8/1989 |
| GB | 2257269 | 1/1993 |
| JP | 58-8522 | 1/1983 |
| JP | 60091858 | 5/1985 |
| JP | 61022752 | 1/1986 |
| JP | 62023361 | 1/1987 |
| JP | 62089470 | 4/1987 |
| JP | 62299277 | 12/1987 |
| JP | 6393516 | 4/1988 |
| JP | 63-181774 | 7/1988 |
| JP | 63217966 | 9/1988 |
| JP | 1089956 | 4/1989 |
| JP | 1135363 | 5/1989 |
| JP | 1158936 | 6/1989 |
| JP | 2107268 | 4/1990 |
| JP | 3081831 | 4/1991 |
| JP | 03-122850 | 12/1991 |
| JP | 4061840 | 2/1992 |
| JP | 4099963 | 3/1992 |
| JP | 4213069 | 8/1992 |
| JP | 4213070 | 8/1992 |
| JP | 4236965 | 8/1992 |
| JP | 5149969 | 6/1993 |
| JP | 5-506806 | 10/1993 |
| JP | 5-309159 | 11/1993 |
| JP | 5-507857 | 11/1993 |
| JP | 6-501179 | 2/1994 |
| JP | 631749 | 4/1994 |
| JP | 6169996 | 6/1994 |
| JP | 6-63224 | 9/1994 |
| JP | 6312313 | 11/1994 |
| JP | 728562 | 5/1995 |
| JP | 7124164 | 5/1995 |
| JP | 7124263 | 5/1995 |
| JP | 7136280 | 5/1995 |
| JP | 7148264 | 6/1995 |
| JP | 7505561 | 6/1995 |
| JP | 7037199 | 7/1995 |
| JP | 7185009 | 7/1995 |
| JP | 7255855 | 10/1995 |
| JP | 7275366 | 10/1995 |
| JP | 751067 | 11/1995 |
| JP | 8-229888 | 9/1996 |
| JP | 8509141 | 10/1996 |
| JP | 8-317988 | 12/1996 |
| JP | 9000164 | 4/1997 |
| JP | 9-276413 | 10/1997 |
| JP | 9-294813 A | 11/1997 |
| JP | 10-118193 | 5/1998 |
| JP | 10328191 | 12/1998 |
| JP | 11-267224 A | 10/1999 |
| JP | 2000-197704 A | 7/2000 |
| JP | 2000-510722 A | 8/2000 |
| JP | 2000-511083 A | 8/2000 |
| JP | 2001-500808 A | 1/2001 |
| JP | 3325828 | 7/2002 |
| JP | 2002-529137 A | 9/2002 |
| JP | 2002-542901 A | 12/2002 |
| JP | 2002-543896 A | 12/2002 |
| JP | 2003-517893 A | 6/2003 |
| JP | 3649604 | 2/2005 |
| JP | 2005-534407 | 11/2005 |
| SU | 712908 | 1/1980 |
| SU | 758421 | 8/1980 |
| SU | 1529365 | 12/1989 |
| WO | WO 90/02520 | 3/1990 |
| WO | WO 91/13364 | 9/1991 |
| WO | WO 92/04072 | 3/1992 |
| WO | WO 92/07619 | 5/1992 |
| WO | WO 93/04722 | 3/1993 |
| WO | WO 93/11313 | 6/1993 |
| WO | WO 95/24236 | 9/1995 |
| WO | WO 96/19255 | 6/1996 |
| WO | WO 97/10022 | 3/1997 |
| WO | WO 97/25914 | 7/1997 |
| WO | WO 97/43949 | 11/1997 |
| WO | WO 97/44083 | 11/1997 |
| WO | WO 97/44086 | 11/1997 |
| WO | WO 98/10694 | 3/1998 |
| WO | WO 99/04847 | 2/1999 |
| WO | WO 99/11313 | 3/1999 |
| WO | WO 00/27303 | 5/2000 |
| WO | WO 00/30710 | 6/2000 |
| WO | WO 00/48645 | 8/2000 |
| WO | WO 00/57943 | 10/2000 |
| WO | WO 00/66199 | 11/2000 |
| WO | WO 00/67845 | 11/2000 |
| WO | WO 00/72907 | 12/2000 |
| WO | WO 01/28620 | 4/2001 |
| WO | WO 01/36034 | 5/2001 |
| WO | WO 01/45773 | 6/2001 |
| WO | WO 01/45912 | 6/2001 |
| WO | WO 01/93920 | 12/2001 |
| WO | WO 02/13682 | 2/2002 |
| WO | WO 02/062540 | 8/2002 |
| WO | WO 03/004086 | 1/2003 |
| WO | WO 03/008148 | 1/2003 |
| WO | WO 2004/012804 | 2/2004 |
| WO | WO 2004/047899 | 6/2004 |

* cited by examiner

MICROMACHINED COMPOSITE GUIDEWIRE STRUCTURE WITH ANISOTROPIC BENDING PROPERTIES

FIELD OF THE INVENTION

The present invention pertains to medical devices, and methods for manufacturing medical devices. More particularly, the present invention pertains to elongated intracorporeal medical devices including a core member having a flattened region.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices. An example medical device may include an elongate core member having a proximal portion and a distal portion. The distal portion may include a distal end and a flattened region. The flattened region may be disposed proximally of the distal end. The flattened region may also have a height and a width. The width may be twice or more as large as the height. A tubular member may be disposed over the distal portion. The tubular member may have a plurality of slots formed therein.

Another example medical device may include an elongate shaft having a preferred bending direction. The shaft may include a core member and a tubular member having a plurality of slots formed therein. The core member may include a hinge region. The hinge region may be disposed proximally of the distal end of the shaft. The hinge region may also have a height and a width. The width may be larger than the height. The preferred bending direction may extend through the height of the flattened region.

An example method for manufacturing a medical device may include providing an elongate core member having a proximal portion and a distal portion, flattening a region of the distal portion to define a flattened region, and disposing a tubular member over the distal portion. The distal portion of the core member may have a distal end and the flattened region may be disposed proximally of the distal end. The flattened region may also have a height and a width. The width may be twice or more as large as the height. The tubular member may have a plurality of slots formed therein.

Another example medical device may include an anisotropic guidewire including a core wire. The core member may include a flattened region. The flattened region may have a height and a width. The width may be larger than the height. A slotted tubular member may be disposed over a portion of the core member. The anisotropic guidewire may have a preferred bending direction. The preferred bending direction may extend through the height of the flattened region.

Another example medical device may include an anisotropic guidewire including a core wire having a distal end. The core member may include a flattened region disposed proximally of the distal end. The flattened region may be disposed proximally of the distal end of the shaft. The flattened region may also have a height and a width. The width may be larger than the height. A slotted tubular member may be disposed over a portion of the core member. The tubular member may be anisotropic in bending. The anisotropic guidewire may have a preferred bending direction. The preferred bending direction may extend through the height of the flattened region.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
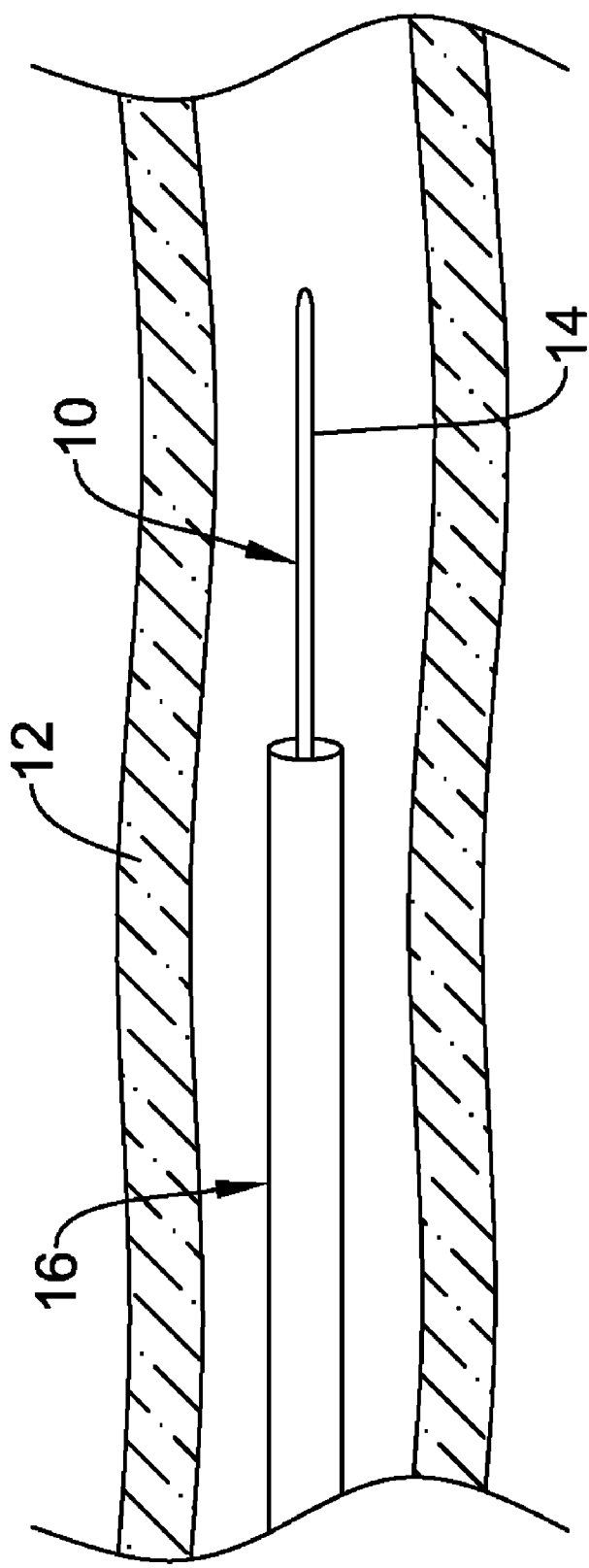
FIG. 1 is a plan view of an example medical device disposed in a blood vessel.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an" and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an example medical device 10, for example a guidewire, disposed in a blood vessel 12. Guidewire 10 may include a distal section 14 that may be generally configured for probing within the anatomy of a patient. Guidewire 10 may be used for intravascular procedures. For example, guidewire 10 may be used in conjunction with another medical device 16, which may take the form of a catheter, to treat and/or diagnose a medical condition. Of course, numerous other uses are known amongst clinicians for guidewires, catheters, and other similarly configured medical devices.

Although medical device 10 is depicted in several of the drawings as a guidewire, it is not intended to be limited to just being a guidewire. Indeed, medical device 10 may take the form of any suitable guiding, diagnosing, or treating device (including catheters, endoscopic instruments, laparoscopic instruments, etc., and the like) and it may be suitable for use at essentially any location and/or body lumen within a patient. For example, medical device/guidewire 10 may be suitable for use in neurological interventions, coronary interventions, peripheral interventions, etc. As such, guidewire 10 may be appropriately sized for any given intervention. For example, guidewire 10 may have an outside diameter of about 0.001 to 0.5 inches or about 0.0015 to 0.05 inches (e.g., about 0.010 to 0.014 inches) for neurological interventions; an outside diameter of about 0.001 to 0.5 inches or about 0.01 to 0.05 inches (e.g., about 0.014 inches) for coronary interventions; or an outside diameter of about 0.01 to 0.5 inches or about 0.02 to 0.05 inches (e.g., about 0.014-0.038 inches) for peripheral interventions. These dimensions, of course, may vary depending on, for example, the type of device (e.g., catheter, guidewire, etc.), the anatomy of the patient, and/or the goal of the intervention. In at least some embodiments, for example, guidewire 10 may be a crossing guidewire that can be used to help a clinician cross an occlusion or stenosis in vessel 12.

Figure 2:
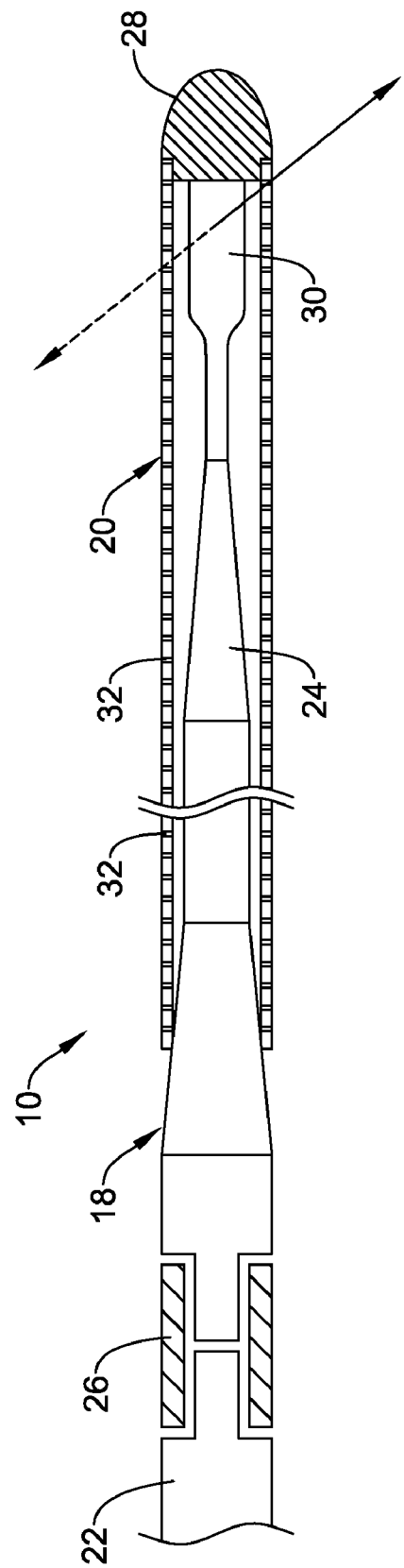
FIG. 2 is a partial cross-sectional view of an example medical device.

FIG. 2 is a partial cross-sectional view of guidewire 10. Here it can be seen that guidewire 10 may include a core member or core wire 18 and a tubular member 20 disposed over at least a portion of core wire 18. Core wire 18 may include a proximal section 22 and a distal section 24. A connector 26 may couple or otherwise attach proximal section 22 to distal section 24. Alternatively, core wire 18 may be a unitary member without a connector. A tip member 28 may also be coupled to core wire 18 and/or tubular member 20 that may define an atraumatic distal tip of guidewire 10. In at least some embodiments, tip member 28 may include a solder ball tip. Alternatively, tip member 28 may include a polymeric material. A coil (not shown) may be disposed in tubular member 20, for example adjacent tip member 28. In at least some embodiments, the coil may take the form of a radiopaque coil.

Often guidewires are designed to be isotropic in bending—i.e., they bend substantially equally in all directions. This may be desirable for a number of reasons. For a number of reasons, however, it may be desirable for a guidewire to be anisotropic in bending—i.e., flexibility in bending differs depending on direction. For example, being anisotropic in bending may allow a guidewire to more easily navigate bends in the anatomy. As such, when advancing through the anatomy an anisotropic guidewire may tend to orient or rotate itself into so that the portions of the guidewire with an increased level of flexibility in bending are aligned with a curve or bend in the anatomy so that the guidewire more easily bends around the curve or bend when advancing through the anatomy.

Guidewire 10 may include one or more structural feature that allows it to be anisotropic in bending. As such, guidewire 10 may have one or more "preferred bending direction(s)" or otherwise may be more easily bent in one direction than in another. In some embodiments, the preferred bending direction is oriented in only a single radial direction along one side of guidewire 10. For example, if the preferred bending direction points only to the left of guidewire 10, guidewire 10 may be more flexible in bending when bending to the left than in essentially any other direction (including, for example, directions perpendicular or orthogonal to the preferred bending direction). In other embodiments, the preferred bending direction may be oriented in opposite radial directions along opposite sides of guidewire 10. For example, if the preferred bending direction points to both the left and right of guidewire 10, guidewire 10 may be more flexible in bending when bending to the left or right than in any other direction (including, for example, directions perpendicular or orthogonal to the preferred bending direction). This later embodiment can be thought of as being similar to "hinge" such that guidewire 10 is more flexible in bending back-and-forth across the hinge.

In at least some embodiments, guidewire 10 may be designed to be more flexible in bending by flattening core wire 18 so as to define a flattened region 30. Flattened region 30 is shown from its broader side in FIG. 2 whereas in FIG. 3, which illustrates guidewire 10 rotated 90 degrees, flattened region 30 is shown from its narrower side. Flattened region 30 may define the preferred bending directions, which are indicated by arrows in FIG. 2-3. For example, in FIG. 2 guidewire 10 is illustrated such that the preferred bending direction extends into and out from the page. Conversely, in FIG. 3 guidewire 10 is illustrated such that the preferred bending direction extends above and below guidewire 10.

The length of flattened region 30 may also vary. In some embodiments, it may be desirable for flattened region 30 to be relatively short so that a preferred bending direction is defined along a relatively short portion of guidewire 10. For example, flattened region 30 may be about 1 centimeter or less in length, or about 2 centimeters or less in length, or about 5 centimeters or less in length, or about 10 centimeters or less in length. Alternatively, flattened region 30 may extend along a greater portion of the length of guidewire 10. It can be appreciate that flattened region 30 may have essentially any suitable length depending of the desired characteristics of guidewire 10 and its intended intervention.

Figure 4:
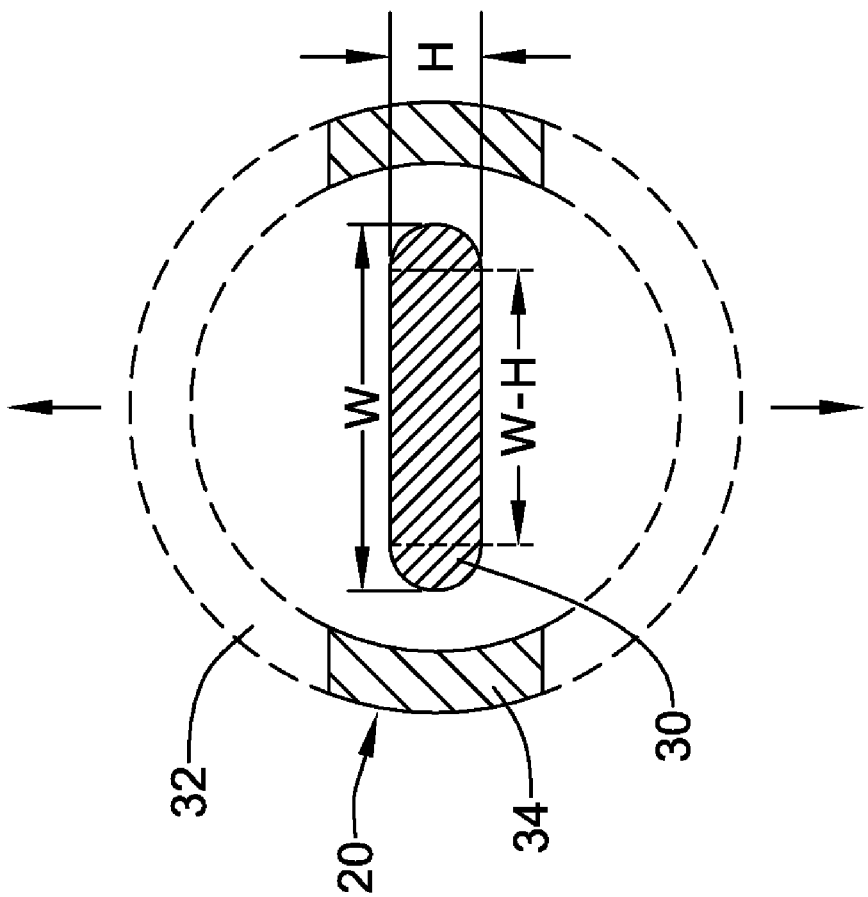
FIG. 4 is a cross-sectional view taken through line 4-4 in FIG. 3.

Turning now to FIG. 4, flattened region 30 is shown in cross-section. Here it can be seen that flattened region 30 may have a width W and a height H. In at least some embodiments, flattened region 30 may have two substantially parallel flat surfaces that extend along width W. This may give flattened region 30 a cross-sectional shape that may be rectangular (or rectangular with rounded edges or "pill-shaped"). These parallel flat surfaces may remain substantially parallel over a length, which may be the entire length of flattened region 30. In other embodiments, these surfaces may converge and/or diverge (e.g., taper) along a portion or all of the length of flattened region 30.

Generally, because width W is longer than height H, guidewire 10 may be more flexible in bending in those directions that are oriented in the direction corresponding to or defining height H. These directions may be thought of as lying within a plane that extends through (and bisects) width W and that are perpendicular to the longitudinal axis of core wire 18 (and/or flattened region 30). For the purposes of this disclosure, these directions may also be understood to extend "through the height H" of flattened region 30. These directions are indicated by arrows in FIG. 4. In orthogonal directions (e.g., orthogonal to the arrows in FIG. 4), guidewire 10 may be less flexible in bending. For the purposes of this disclosure, these orthogonal directions may be understood to extend "through the width W" of flattened region 30.

It can be appreciated that the size of width W relative to height H can vary depending upon the degree to which flattened region 30 is flattened. In some embodiments, width W may be about 1.1 times as large as height H or more. In still other embodiments, width W may be about 1.4 as large as height H or more. In still other embodiments, width W may be about 2 times as large as height H or more. In still other embodiments, width W may be about 3 times as large as height H or more. In still other embodiments, width W may be about 5 times as large as height H or more. In still other embodiments, width W may be about 8 times as large as height H or more. In still other embodiments, width W may be about 20 times as large as height H or more. In still other embodiments, width W may be about 75 times as large as height H or more.

It can be appreciated that as the length of width W increases relative to height H, the greater the difference in flexibility in bending in the preferred bending direction relative to the orthogonal direction. In order to attempt to understand the relative extent to which flexibly in bending changes between the preferred bending direction (e.g., aligned with the arrows) and in directions orthogonal to the preferred bending direction, the moments of inertia (I) can be calculated for the preferred bending direction and for the direction orthogonal to the preferred bending direction (see, for example, Gere and Timoshenko, "Mechanics of Materials", $2^{nd}$ Edition, pp 707, 724, 726, the entire disclosure of which is herein incorporated by reference). In making these calculations, an assumption is made that flattened region 30 has semicircular edges and conserves cross-sectional area. The moment of inertia in the preferred bending direction ($I_p$) may be simple because rotation is about a centroid. Thus, $I_p$ may be equal to:

I(rectangle)+2*I(semicircle).

The parallel axis theorem may be used to find the moment of inertia of the two semicircles about the center of core wire 18 such that $I_p$ may be equal to:

$((W-H)*H^3)/12+\pi*H^4/64)$.

The moment of inertia orthogonal to the preferred bending direction ($I_o$) may be equal to:

I(rectangle)2*I(semicircle)+Area(semicircle)*
(distance to semicircle)$^2$)=(H*(W-H)$^3$)/12+2*
(($\pi$*(H/2)$^4$/8)+((W-H)/2)$^2$*($\pi$*(H/2)$^2$/2)).

Note that width W may be equal to:

H+$\pi$/4((Core starting diameter$^2$/H)-H).

Using a core starting diameter of 0.0100 inches, $I_p$ and $I_o$ can be calculated across a range of flattened widths W and heights H. The results of these calculations are listed in Table 1.

Based on these calculations, it can be seen that as the extent of flattening increases (i.e., as width W increase relative to height H), the ratio of $I_p/I_o$ increases. It can be seen from the calculations that flattening a 0.0100 inch core wire 18 to 0.005 inches may result in a 9-fold change in bending flexibility between bending guidewire 10 in directions extending through height H (e.g., the preferred bending direction) as opposed to directions extending through width W. Similar calculations can be made for embodiments where a different core starting diameter is used and/or where differing amounts of flattening are utilized.

Figure 3:
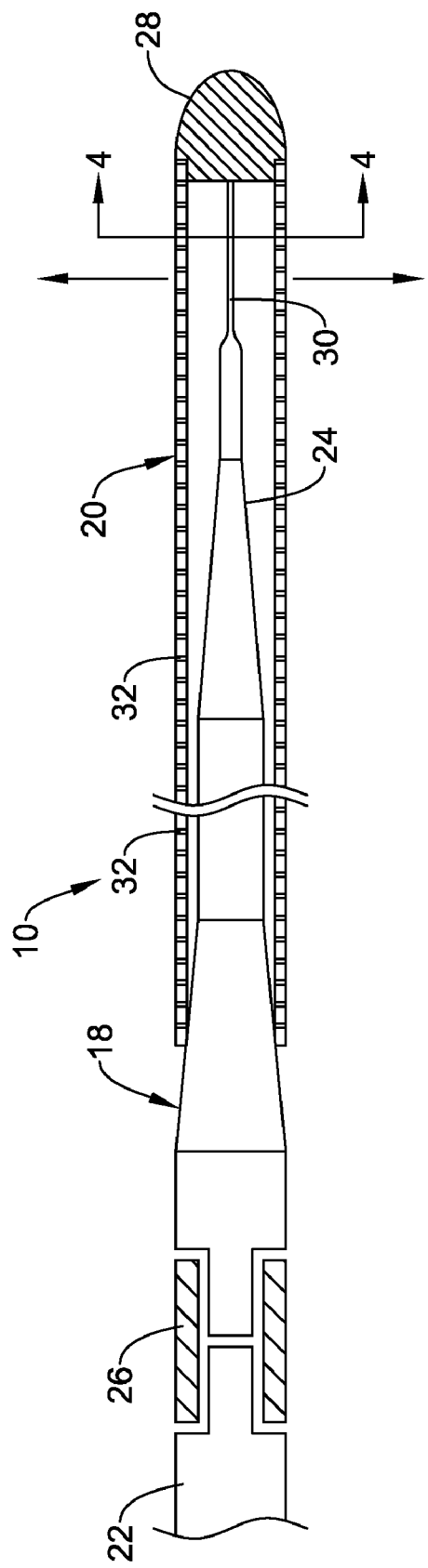
FIG. 3 is a partial cross-section view of the device illustrated in FIG. 2 rotated ninety degrees about its longitudinal axis.
Figure 5:
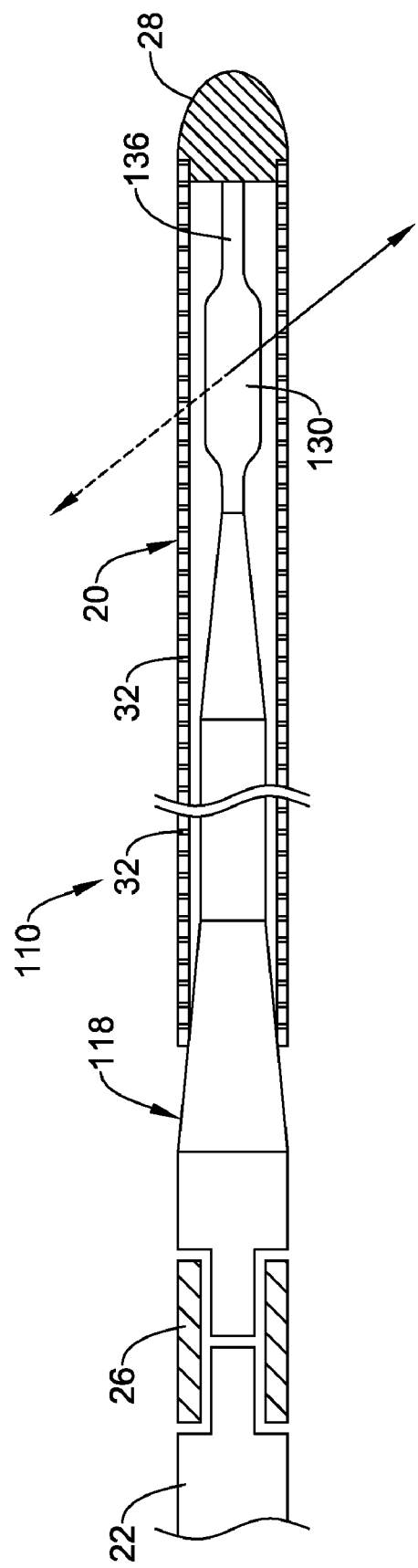
FIG. 5 is a partial cross-sectional view of another example medical device.

Although FIGS. 2-3 depict flattened region 30 as being disposed at the distal end of core wire 18, this is not intended to be limiting. For example, FIG. 5 illustrates guidewire 110 that may be similar to guidewire 10 except that core wire 118 includes flattened region 130 that is disposed proximal of the distal end of core wire 118. As such, a distal region 136 (which may have a substantially round cross-sectional shape) of core wire 118 may extend distally from flattened region 130. In at least some embodiments, flattened region 130 is flanked on both ends by portions of core wire 118 that have a substantially round cross-sectional shape.

By placing flattened region 130 a distance proximal of the distal end of core wire 118, the "hinge" that may be defined by flattened region 130 may be disposed at a place where it may be more practical for navigating the anatomy. For example, placing flattened region 130 proximally of the distal end of core wire 118 may allow a suitable portion of guidewire 110 to bend around the anatomy. The length of distal region 136 (and/or the distance that flattened region 130 is disposed proximally of the distal end of core wire 118) may vary. For example, distal region 136 may be about 1 centimeter or less. In other embodiments, distal region 136 may be about 1 centimeter or more. In still other embodiments, distal region 136 may be about 2 centimeters or more. In still other embodiments, distal region 136 may be about 3 centimeters or more. In still other embodiments, distal region 136 may be about 4 centimeters or more. In still other embodiments, distal region 136 may be about 5 centimeters or more.

In addition to variations in the location of flattened region 30/130, other structures may be altered to provide guidewire 10/110 with desirable features. For example, tubular member 20 may be altered. In at least some embodiments, tubular member 20 includes a plurality of cuts, apertures, and/or slots 32 formed therein. Slots 32 can be formed by methods such as micro-machining, saw-cutting (e.g., using a diamond grit embedded semiconductor dicing blade), laser cutting, electron discharge machining, grinding, milling, casting, molding, chemically etching or treating, or other known methods,

TABLE 1

Bending moments in the preferred bending direction and in the direction orthogonal to the preferred bending direction.

| Core starting Diameter (inches) | Core height H (inches) | Core width W (inches) | Moment of inertia $I_p$ | Moment of inertia $I_o$ | Ratio of $I_p/I_o$ |
|---|---|---|---|---|---|
| 0.0100 | 0.00900 | 0.01066 | 4.2279E−10 | 3.69205E−10 | 0.87 |
| 0.0100 | 0.00800 | 0.01153 | 3.51858E−10 | 3.87463E−10 | 1.10 |
| 0.0100 | 0.00700 | 0.01272 | 2.81418E−10 | 5.42183E−10 | 1.93 |
| 0.0100 | 0.00600 | 0.01438 | 2.14414E−10 | 8.53703E−10 | 3.98 |
| 0.0100 | 0.00500 | 0.01678 | 1.53398E−10 | 1.39326E−09 | 9.08 |
| 0.0100 | 0.00400 | 0.02049 | 1.00531E−10 | 2.36275E−09 | 23.50 |
| 0.0100 | 0.00300 | 0.02682 | 5.75795E−11 | 4.38737E−09 | 76.20 |
| 0.0100 | 0.00200 | 0.03970 | 2.59181E−11 | 1.00468E−08 | 387.64 |
| 0.0100 | 0.00100 | 0.07875 | 6.52862E−12 | 4.03608E−08 | 6182.13 | and the like. In some such embodiments, the structure of the tubular member 20 is formed by cutting and/or removing portions of the tube to form slots 32. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 10 may include forming slots 32 in tubular member 20 using any of these or other manufacturing steps.

Slots 32 may be provided to enhance the flexibility of tubular member 20 while still allowing for suitable torque transmission characteristics. Slots 32 may be formed such that one or more rings and/or turns interconnected by one or more segments and/or beams 34 are formed in tubular member 20, and such rings and beams 34 may include portions of tubular member 20 that remain after slots 32 are formed in the body of tubular member 20. Such an interconnected ring structure may act to maintain a relatively high degree of torsional stiffness, while maintaining a desired level of lateral flexibility. In some embodiments, some adjacent slots 32 can be formed such that they include portions that overlap with each other about the circumference of tubular member 20. In other embodiments, some adjacent slots 32 can be disposed such that they do not necessarily overlap with each other, but are disposed in a pattern that provides the desired degree of lateral flexibility.

Various embodiments of arrangements and configurations of slots 32 are contemplated. In some embodiments, at least some, if not all of slots 32 are disposed at the same or a similar angle with respect to the longitudinal axis of the tubular member 20. As shown, slots 32 can be disposed at an angle that is perpendicular, or substantially perpendicular, and/or can be characterized as being disposed in a plane that is normal to the longitudinal axis of tubular member 20. However, in other embodiments, slots 32 can be disposed at an angle that is not perpendicular, and/or can be characterized as being disposed in a plane that is not normal to the longitudinal axis of tubular member 20. Additionally, a group of one or more slots 32 may be disposed at different angles relative to another group of one or more slots 32. The distribution and/or configuration of slots 32 can also include, to the extent applicable, any of those disclosed in U.S. Pat. Publication No. US 2004/0181174, the entire disclosure of which is herein incorporated by reference.

Figure 6:
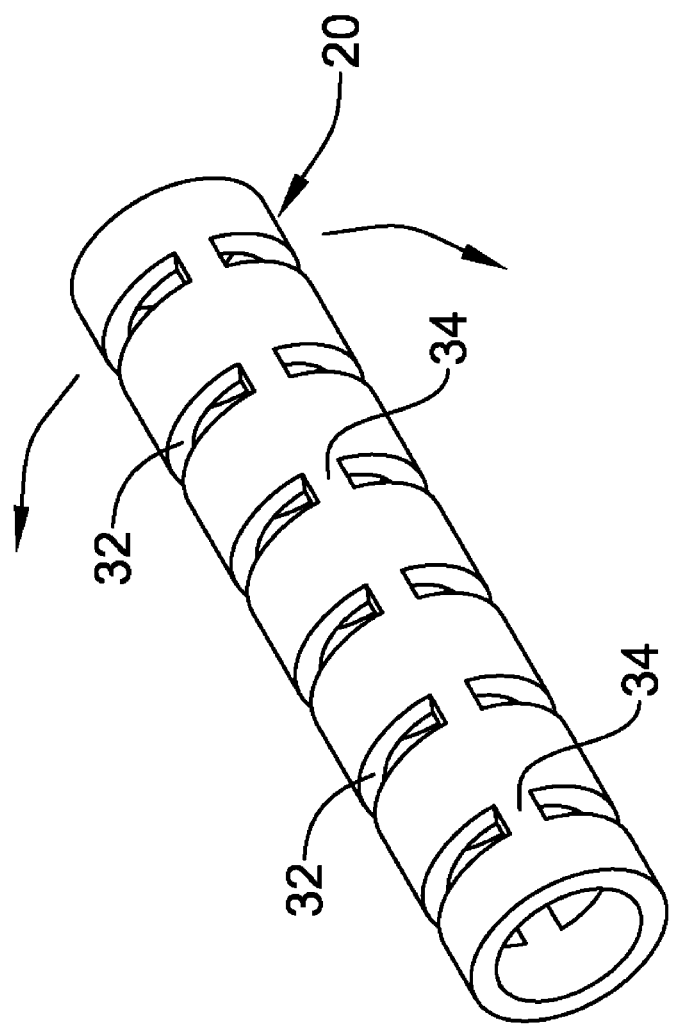
FIG. 6 is a perspective view of an example tubular member for use in a medical device.
Figure 7:
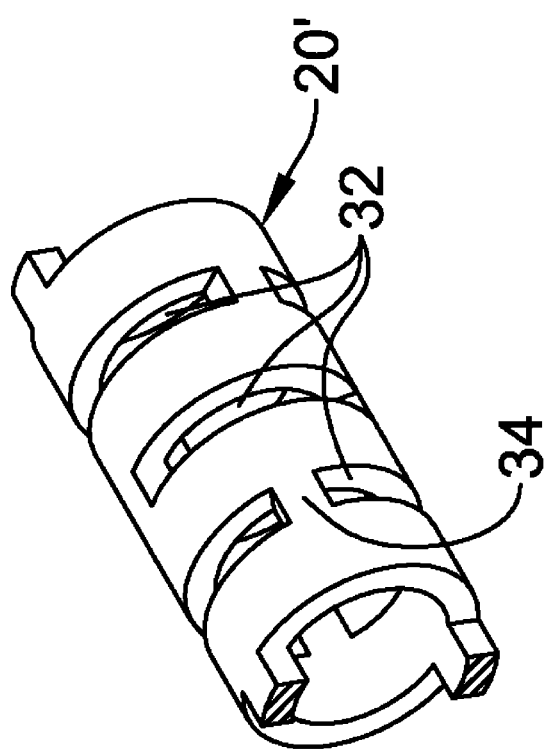
FIG. 7 is a perspective view of another example tubular member for use in a medical device.

Additionally, slots 32 can be arranged along the length of, or about the circumference of, tubular member 20 to achieve desired properties. For example, adjacent slots 32, or groups of slots 32, can be arranged in a symmetrical pattern, such as being disposed essentially equally on opposite sides about the circumference of tubular member 20 as illustrated in FIG. 6. Tubular members having this arrangement may be anisotropic in bending such that they tend to have greater flexibility in bending in directions aligned with slots 32 (indicated by arrows in FIG. 6) and less flexible in bending in other directions including orthogonal directions. In some embodiments, anisotropic tubular member 20 may be configured so that both flattened region 30/130 and slots 32 define aligned and/or parallel preferred bending directions. This arrangement is depicted in FIG. 4. Alternatively, anisotropic tubular member 20 and flattened region 30/130 may define misaligned preferred bending directions. In some other embodiments, slots 32 or groups of slots 32 can be rotated by an angle relative to each other about the longitudinal axis of tubular member 20', for example, as illustrated in FIG. 7. According to this embodiment, tubular member 20' may be isotropic. It can be appreciated that essentially any suitable tubular member 20/20' may be utilized in combination with any suitable flattened region 30/130 without departing from the spirit of the invention.

Additionally, adjacent slots 32, or groups of slots 32, may be equally spaced along the length of tubular member 20, or can be arranged in an increasing or decreasing density pattern, or can be arranged in a non-symmetric or irregular pattern. Other characteristics, such as slot size, slot shape and/or slot angle with respect to the longitudinal axis of tubular member 20, can also be varied along the length of tubular member 20 in order to vary the flexibility or other properties. In other embodiments, moreover, it is contemplated that the portions of the tubular member, such as a proximal section 26, or a distal section 28, or the entire tubular member 20, may not include any such slots 32.

As suggested above, slots 32 may be formed in groups of two, three, four, five, or more slots 32, which may be located at substantially the same location along the axis of tubular member 20. Within the groups of slots 32, there may be included slots 32 that are equal in size (i.e., span the same circumferential distance around tubular member 20). In some of these as well as other embodiments, at least some slots 32 in a group are unequal in size (i.e., span a different circumferential distance around tubular member 20). Longitudinally adjacent groups of slots 32 may have the same or different configurations. For example, some embodiments of tubular member 20 include slots 32 that are equal in size in a first group and then unequally sized in an adjacent group. It can be appreciated that in groups that have two slots 32 that are equal in size, the beams (i.e., the portion of tubular member 20 remaining after slots 32 are formed therein) are aligned with the center of tubular member 20. Conversely, in groups that have two slots 32 that are unequal in size, the beams are offset from the center of tubular member 20. Some embodiments of tubular member 20 include only slots 32 that are aligned with the center of tubular member 20, only slots 32 that are offset from the center of tubular member 20, or slots 32 that are aligned with the center of tubular member 20 in a first group and offset from the center of tubular member 20 in another group. The amount of offset may vary depending on the depth (or length) of slots 32 and can include essentially any suitable distance.

The materials that can be used for the various components of guidewire 10/110 may include those commonly associated with medical devices. For example, core wire 18, and/or tubular member 20, and/or connector 26, and/or tip member 28, and the like may be made from a metal, metal alloy, polymer (some examples of which are disclosed below), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof, and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of core wire 18, tubular member 20, tip member 28, etc. may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of MRI compatibility is imparted into guidewire 10. For example, to enhance compatibility with Magnetic Resonance Imaging (MRI) machines, it may be desirable to make core wire 18 and/or tubular member 20, or other portions of the guidewire 10, in a manner that would impart a degree of MRI compatibility. For example, core wire 18 and/or tubular member 20, or portions thereof, may be made of a material that does not substantially distort the image and create substantial artifacts (artifacts are gaps in the image). Certain ferromagnetic materials, for example, may not be suitable because they may create artifacts in an MRI image. Core wire 18 and/or tubular member 20, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Referring now to core wire 18, the entire core wire 18 can be made of the same material along its length, or in some embodiments, can include portions or sections made of different materials. In some embodiments, the material used to construct core wire 18 is chosen to impart varying flexibility and stiffness characteristics to different portions of core wire 18. For example, proximal section 22 and distal section 24 of core wire 18 may be formed of different materials, for example materials having different moduli of elasticity, resulting in a difference in flexibility. In some embodiments, the material used to construct proximal section 22 can be relatively stiff for pushability and torqueability, and the material used to construct distal section 24 can be relatively flexible by comparison for better lateral trackability and steerability. For example, proximal section 22 can be formed of straightened 304v stainless steel wire or ribbon and distal section 24 can be formed of a straightened super elastic or linear elastic alloy, for example a nickel-titanium alloy wire or ribbon.

In embodiments where different portions of core wire 18 are made of different materials, the different portions can be connected using any suitable connecting techniques and/or with connector 26. For example, the different portions of core wire 18 can be connected using welding (including laser welding), soldering, brazing, adhesive, or the like, or combinations thereof. These techniques can be utilized regardless of whether or not connector 26 is utilized. Connector 26 may include any structure generally suitable for connecting portions of a guidewire. One example of a suitable structure includes a structure such as a hypotube or a coiled wire which has an inside diameter sized appropriately to receive and connect to the ends of the proximal portion and the distal portion. Essentially any suitable configuration and/or structure can be utilized for connector 26 including those connectors described in U.S. Pat. Nos. 6,918,882 and 7,071,197 and/or in U.S. Patent Pub. No. US 2006-0122537, the entire disclosures of which are herein incorporated by reference.

A sheath or covering (not shown) may be disposed over portions or all of core wire 18 and/or tubular member 20 that may define a generally smooth outer surface for guidewire 10. In other embodiments, however, such a sheath or covering may be absent from a portion of all of guidewire 10, such that tubular member 20 and/or core wire 18 may form the outer surface. The sheath may be made from a polymer or any other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6% LCP.

In some embodiments, the exterior surface of the guidewire 10 (including, for example, the exterior surface of core wire 18 and/or the exterior surface of tubular member 20) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of core wire 18 and/or tubular member, or other portions of device 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The same may be true of tip member 30. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device, comprising:
   an elongate core member having a proximal portion and a distal portion;
   wherein the distal portion includes a distal end and a flattened region disposed proximally of the distal end, the flattened region having a height and a width, the width being twice or more as large as the height;
   a tubular member disposed over the distal portion, the tubular member having a plurality of slots formed therein; and
   wherein the flattened region of the core member individually has anisotropic bending properties and includes at least one preferred bending direction, wherein the tubular member individually has anisotropic bending properties and includes at least one preferred bending direction, and wherein the tubular member is disposed over the distal portion such that the preferred bending direction of the flattened region of the core member is aligned with the preferred bending direction of the tubular member.

2. The medical device of claim 1, wherein the medical device is more flexible in a direction extending through the height of the core wire than in another direction extending through the width of the core wire.

3. The medical device of claim 1, wherein the tubular member is isotropic in bending.

4. The medical device of claim 1, wherein the proximal portion of the core member has a substantially round cross-sectional shape.

5. The medical device of claim 1, wherein the flattened region is disposed at least one centimeter proximally of the distal end of the core member.

6. The medical device of claim 1, wherein the flattened region is disposed more than one centimeter proximally of the distal end of the core member.

7. A guidewire, comprising:
an elongate shaft having a preferred bending direction, the shaft including a core member and a tubular member having a plurality of slots formed therein;
wherein the core member includes a hinge region disposed proximally from a distal end of the core member and a distal region extending between the hinge region and the distal end of the core member, the hinge region having a height and a width, the width being larger than the height;
wherein the distal region of the core member has a substantially circular cross-sectional shape;
a tip member attached to the distal end of the core member; and
wherein the preferred bending direction extends through the height of the hinge region.

8. The guidewire of claim 7, wherein the width is two or more times larger than the height.

9. The guidewire of claim 7, wherein the width is three or more times larger than the height.

10. The guidewire of claim 7, wherein the width is four or more times larger than the height.

11. The guidewire of claim 7, wherein the width is five or more times larger than the height.

12. The guidewire of claim 7, wherein the hinge region is disposed at least one centimeter proximally of the distal end of the core member.

13. The guidewire of claim 7, wherein the hinge region is disposed more than one centimeter proximally of the distal end of the core member.

14. A method for manufacturing a medical device, the method comprising:
providing an elongate core member having a proximal portion and a distal portion;
flattening a region of the distal portion to define a flattened region, the flattened region having a height and a width, the width being twice or more as large as the height;
wherein the distal portion of the core member has a distal end and wherein the flattened region is disposed proximally of the distal end and between the flattened region and the distal end the core member has a substantially circular cross-sectional shape;
disposing a tubular member over the distal portion, the tubular member having a plurality of slots formed therein; and
attaching a tip member to the distal end of the distal portion of the core member.

* * * * *